US009081696B2

(12) United States Patent
Smith

(10) Patent No.: US 9,081,696 B2
(45) Date of Patent: Jul. 14, 2015

(54) METHODS AND SYSTEMS FOR SECURE INTEROPERABILITY BETWEEN MEDICAL DEVICES

(75) Inventor: Todd E. Smith, Hopedale, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/817,575

(22) PCT Filed: Aug. 24, 2010

(86) PCT No.: PCT/US2010/046460
§ 371 (c)(1),
(2), (4) Date: Feb. 19, 2013

(87) PCT Pub. No.: WO2012/026922
PCT Pub. Date: Mar. 1, 2012

(65) Prior Publication Data
US 2013/0151739 A1 Jun. 13, 2013

(51) Int. Cl.
| G06F 3/00 | (2006.01) |
| G06F 13/28 | (2006.01) |
| G06F 13/00 | (2006.01) |
| G06F 5/00 | (2006.01) |
| G06F 13/10 | (2006.01) |
| H04W 4/00 | (2009.01) |
| G06F 19/00 | (2011.01) |
| H04L 29/06 | (2006.01) |

(52) U.S. Cl.
CPC ............ *G06F 13/10* (2013.01); *G06F 19/3412* (2013.01); *H04L 69/18* (2013.01); *H04W 4/005* (2013.01); *G06F 19/321* (2013.01); *G06F 19/3418* (2013.01); *H04L 69/16* (2013.01)

(58) Field of Classification Search
CPC .... G06F 3/1206; G06F 3/1245; G06F 19/324
USPC .................................. 710/33, 11, 22, 30, 58
See application file for complete search history.

(56) References Cited

U.S. PATENT DOCUMENTS

| 7,730,242 | B2 * | 6/2010 | Tsuchiya ........................ 710/72 |
| 7,941,575 | B2 * | 5/2011 | Roy et al. ........................ 710/29 |
| 8,082,336 | B1 * | 12/2011 | Heath ............................ 709/223 |
| 8,136,085 | B2 * | 3/2012 | Skillman et al. ............... 717/100 |
| 8,555,371 | B1 * | 10/2013 | Signaoff et al. .................. 726/12 |
| 8,605,730 | B2 * | 12/2013 | Signaoff et al. ............. 370/395.5 |
| 2005/0149624 | A1 * | 7/2005 | Jakubiec et al. ............... 709/217 |
| 2009/0177769 | A1 * | 7/2009 | Roberts ......................... 709/224 |
| 2011/0145373 | A1 * | 6/2011 | Awad et al. ................... 709/220 |

* cited by examiner

*Primary Examiner* — Idriss N Alrobaye
*Assistant Examiner* — Getente A Yimer
(74) *Attorney, Agent, or Firm* — Chapin IP Law, LLC

(57) ABSTRACT

An interface device is configured to provide one or more links to first-party medical devices, each of which communicates using a proprietary protocol. The interface device can translate between the proprietary protocol and a second protocol that is accessible via a second link to the interface device. Details of the second protocol can be provided to third parties for configuring third-party medical devices to connect to the interface device via the second link. Using the second link, one or more third-party medical devices can send information to and/or receive information from the first-party medical devices without the need for the third-party device (or devices) to have any information about the proprietary protocol(s) of the first-party medical device(s). The first-party medical devices can include surgical tools and related support equipment and the third-party medical device can include a control station used to monitor and control the tools and support equipment.

36 Claims, 6 Drawing Sheets

METHODS AND SYSTEMS FOR SECURE INTEROPERABILITY BETWEEN MEDICAL DEVICES

BACKGROUND

Processor-based devices continue to proliferate and the medical field is no exception to this ongoing trend. For example, a medical procedure can involve use of one or more processor-based medical devices. These medical devices can include, but are not limited to, surgical tools, patient monitoring equipment, and patient support devices. The processor of each device can be used for device control, data collection and exchange, and other tasks.

The medical devices used in the procedure may be provided by a single manufacturer or multiple different manufacturers. In either case an end user of a medical device may have limited options if he or she wishes to interface the device or device(s) from one manufacturer with a device or devices of another manufacturer. Particularly, each manufacturer of medical devices may use a unique communications protocol for data collection and exchange. Usually, the details of these protocols are proprietary. To protect their competitive position and to ensure high-quality operation, manufactures are understandably reluctant to share proprietary information with competitors.

SUMMARY

Embodiments of the invention discussed herein may allow a medical device manufacturer to meet interoperability needs of end users without the need to share proprietary information. In one illustrative embodiment, an interface device is configured to provide one or more links to first-party medical devices, each of which communicates using a proprietary protocol. The interface device can be configured to translate between the proprietary protocol and a second protocol that is accessible via a second link to the interface device. Details of the second protocol can be provided to third parties for configuring third-party medical devices to connect to the interface device via the second link. Using the second link, one or more third-party medical devices can send information to and/or receive information from the first-party medical devices without the need for the third-party device (or devices) to have any information about the proprietary protocol(s) of the first-party medical device(s).

In one embodiment, the first-party medical devices are a plurality of surgical tools and related support equipment and the third-party medical device is a control station used to monitor and control the tools and support equipment. The tools and support equipment can be connected to the interface device via respective connections that use a proprietary physical communication protocol. For example, in one embodiment the tools use a proprietary serial communication protocol. The interface device can translate between the serial protocol(s) for the first-party devices and a second protocol that is available to the control station over an Ethernet connection.

An illustrative method comprises using the interface device to poll a first medical device over a first interface and to act as a server for client requests from the third-party device(s) received via a second link. For example, the second link may comprise a network connection such as a TCP/IP protocol stack provided over an Ethernet or other network link. The interface device can communicate with each of the first-party medical devices via a respective first interface while the interface device is itself in communication with the third-party device(s) via the second interface. The interface device can make data from respective first-party medical devices available in response to client requests made using a network port (such as a TCP/IP port) corresponding to each respective first-party medical device. As another example, the interface device can receive data such as commands and settings for a particular first-party medical device, with the intended device identified according to the port over which the commands and settings are provided. In response, the interface device can convert the data to a corresponding first-party device protocol and transmit the data via the first interface.

These illustrative embodiments are mentioned not to limit or define the limits of the present subject matter, but to provide examples to aid understanding thereof. Illustrative embodiments are discussed in the Detailed Description, and further description is provided there. Advantages offered by various embodiments may be further understood by examining this specification and/or by practicing one or more embodiments of the claimed subject matter.

BRIEF DESCRIPTION OF THE DRAWINGS

A full and enabling disclosure is set forth more particularly in the remainder of the specification. The specification makes reference to the following appended figures.

DETAILED DESCRIPTION

Reference will now be made in detail to various and alternative exemplary embodiments and to the accompanying drawings. Each example is provided by way of explanation, and not as a limitation. It will be apparent to those skilled in the art that modifications and variations can be made. For instance, features illustrated or described as part of one embodiment may be used on another embodiment to yield a still further embodiment. Thus, it is intended that this disclosure includes modifications and variations as come within the scope of the appended claims and their equivalents.

In the following detailed description, numerous specific details are set forth to provide a thorough understanding of the claimed subject matter. However, it will be understood by those skilled in the art that claimed subject matter may be practiced without these specific details. In other instances, methods, apparatuses or systems that would be known by one of ordinary skill have not been described in detail so as not to obscure the claimed subject matter.

Figure 1:
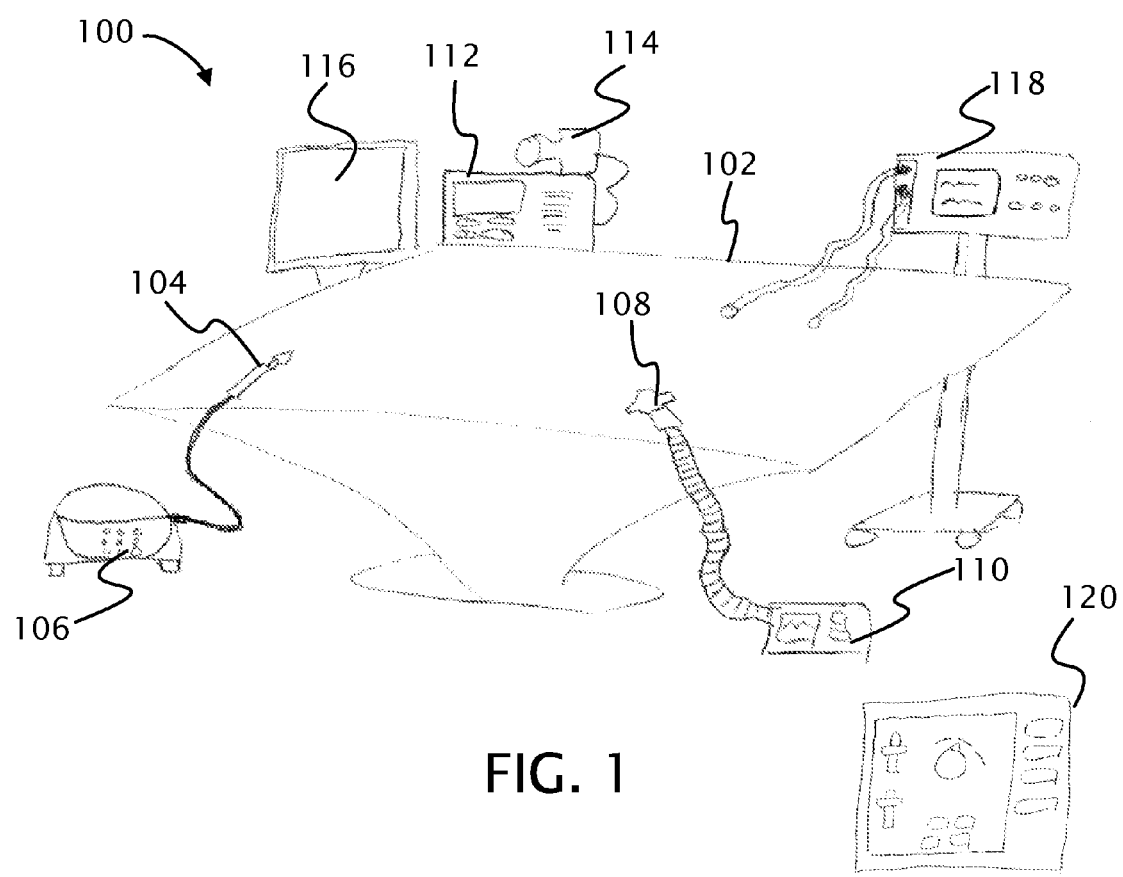
FIG. 1 is a diagram showing an exemplary group of medical devices.

FIG. 1 is a diagram showing an exemplary group 100 of medical devices. In this example, a table 102 or other support is provided to receive a patient (not shown) who is to undergo a medical procedure. For example, procedures such as arthroscopy and endoscopy may utilize a number of medical devices, though it will be recognized that the present subject matter can be used in the context of any type of equipment used in any type of medical procedure.

In this example, the plurality of devices include an ablation probe 104 that is used to apply microwave or other energy to tissue during the procedure. Ablation probe 104 includes a processor-controlled energy source 106. A shaver handpick 108 along with driver 110 may be used in arthroscopic surgery and other procedures to shave bone or other structures, with power and torque provided by driver 110 as directed by a processor or microcontroller in response to user inputs. A camera system 112 and camera head 114 may be used along with monitor 116 to view anatomical features of the patient during a procedure. Fluid management system 118 may be used to control the volume of one or more fluids in a surgical cavity during the procedure by use of one or more pumps, valves, and the like directed by operation of a processor of system 118.

Still further equipment (not shown) can be used to monitor the patient's vital signs during the procedure, to provide fluids, ventilation, etc. Some or all of this equipment may be controlled by processors such as microprocessors, microcontrollers, and other devices. A medical device may feature one or more microprocessors and the device architecture is not intended to be limiting.

Medical devices 100 may be designed to provide data and/or receive commands over a data interface. For example, the devices may be provided with serial or other ports so that the devices can be linked to one another and/or a control system 120 to provide data, receive commands, etc. Control system 120 may be configured to provide a user interface that can be adapted to control different types of devices. For example, control system 120 may comprise a computer workstation, standalone device, or some other type of device that can provide a graphical user interface and/or touch interface. As another example, control system 120 may feature buttons, knobs, sliders, and other mechanical interfaces that can be mapped to provide devices input along with indicators lights, dials, light emitting diode (LED) outputs, and the like to provide device outputs.

As noted above, problems may arise when an end user wishes to use devices provided by different manufacturers. Particularly, although devices 100 may include serial or other communications ports, devices from one manufacturer may communicate using a proprietary protocol that is not available to other manufacturers. For example, a manufacturer of devices 104, 106, 108, 110, 112, 114, 116, and 118 (the "first-party" manufacturer) may wish to allow its devices to operate with a control system 120 provided by a different manufacturer (a "third-party" manufacturer), but may be unable to share the details of the communications protocol(s) used by devices 104-118. In this example, all of devices 104-118 are provided by the same manufacturer. However, as another example, some of devices 104-118 may be provided by the third-party manufacturer and may be able to interface directly with the third-party manufacturer's control system 120. The user may wish to use at least one device provided by the first-party manufacturer, and can do so using interface device 122.

As another example, the first-party manufacturer may actually provide devices provided by another party (a "fourth party") and the first-party manufacturer may have access to the control protocol(s) of the fourth party devices for interoperability purposes. For purposes of the examples herein the "fourth party" devices can be treated the same as the first-party devices.

Figure 2:
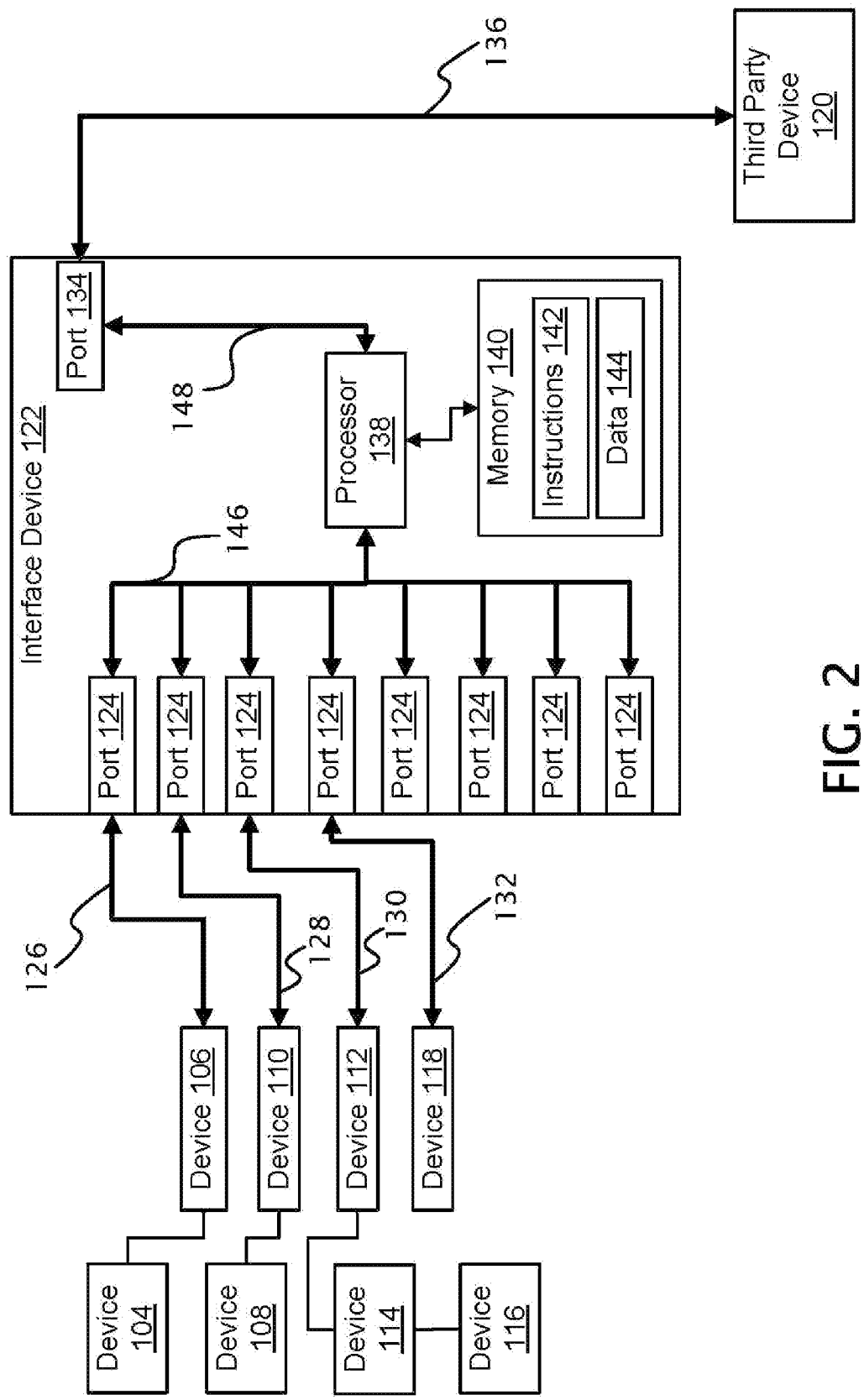
FIG. 2 is a diagram showing an example of how the first-party manufacturer can allow its devices to operate with third-party hardware through use of an embodiment of an interface device.

FIG. 2 is a diagram showing an example of how the first-party manufacturer can allow its devices to operate with third-party hardware. In this example an interface device 122 is provided to provide a bridge between devices 104-118 and third-party controller 120. Interface device 122 features a plurality of first hardware connection ports 124 which are configured to connect to corresponding data interfaces of devices 106, 110, 112 and 118 over links 126, 128, 130, and 132, respectively. Interface device 122 also features a second hardware connection port 134 that provides a link 136 to third-party controller 120. In this example, devices 104, 108, 114, and 116 are linked to respective base units and are not independently linked to interface device 122, but it will be understood that the particular group of devices and data flow arrangement amongst the devices is shown for purposes of example only. Embodiments include the use of more or fewer hardware connection ports 124 than the number shown in this example.

Interface device 122 comprises a processor 138 and memory 140. Memory 140 embodies program instructions 142 that can be carried out by processor 138 to translate between one or more protocols used by devices 104-118 and a protocol used by device 120. Data 144 is shown to represent data received from one or more of devices 104-118, data received from device 120, working data of interface device 122, and/or data to be sent to one or more of devices 104-120. Processor 138 can comprise any suitable processing device or devices including, but not limited to microprocessors, microcontrollers, and the like.

In one embodiment, processor 138 comprises a multitasking processor that can access a first bus 146 to send/receive data via hardware connection ports 124 while a second bus 148 is used to send/receive data via hardware connection port 134. Port 134 may, for example, comprise an RJ45 port, with processor 138 configured to provide an Ethernet (IEEE 802.3) network interface, although a coprocessor such as a network controller can be used to manage the network interface in some embodiments. In addition to or instead of an RJ45 port, other embodiments might utilize any suitable serial or wireless interface.

Each port 124 can be configured to provide a suitable physical link to its corresponding medical device. Although all ports are shown here as "port 124," it will be understood that the various instances labeled as port 124 could vary in construction (e.g., number and type of physical connectors). For instance, depending on the first-party manufacturer and/or the particular devices, ports 124 may comprise serial ports of the same or different configuration, such as RS-232 connections, USB connections, etc. As another example, one or more ports 124 could comprise parallel ports, RJ45 or other ports, or any other physical link. Wireless technology (e.g., IEEE 802.11, 802.16, or another radio technology) could be used in providing the physical link to one or more of ports 124 and/or port 134 as well, provided the wireless technology was suitable for use in a medical environment. Other examples of physical connections that can be used on either or both sides include Ethernet, RS-485, RS-422, and Infrared (IR).

Although not shown here, interface device 122 can include additional features. For example, if one or more of devices 104-120 is configured to draw power on its data interface, then the corresponding port(s) of interface device 122 can be configured to provide power (e.g., +5V DC if required) from a suitable power supply connected to interface device 122. Additionally, although a single port 136 is shown, interface device 122 could support multiple physical connections for relaying data and commands via the second protocol.

In any event, program instructions 142 configure processor 138 to communicate with devices 106, 110, 112, and 118 according to the proprietary first-party protocol(s) used over each respective link 126, 128, 130, and 132. The first-party protocol(s) can include any number of communications protocols used by the devices. In some cases all devices may use the same proprietary protocol. On the other hand, in some cases one or more of devices 106, 110, 112, and 118 may have a device-specific communications protocol.

Regardless of the number or type of first-party communication protocols, program instructions 142 can enable processor 138 to send and receive data and/or commands according to the protocols. Program instructions 142 further configure processor 138 to communicate with device 120 using a second communications protocol, the details of which can be revealed to third parties to allow device 120 to interoperate with devices 106-118. Examples of this communication will be discussed below in conjunction with FIGS. 3-5.

Figure 3:
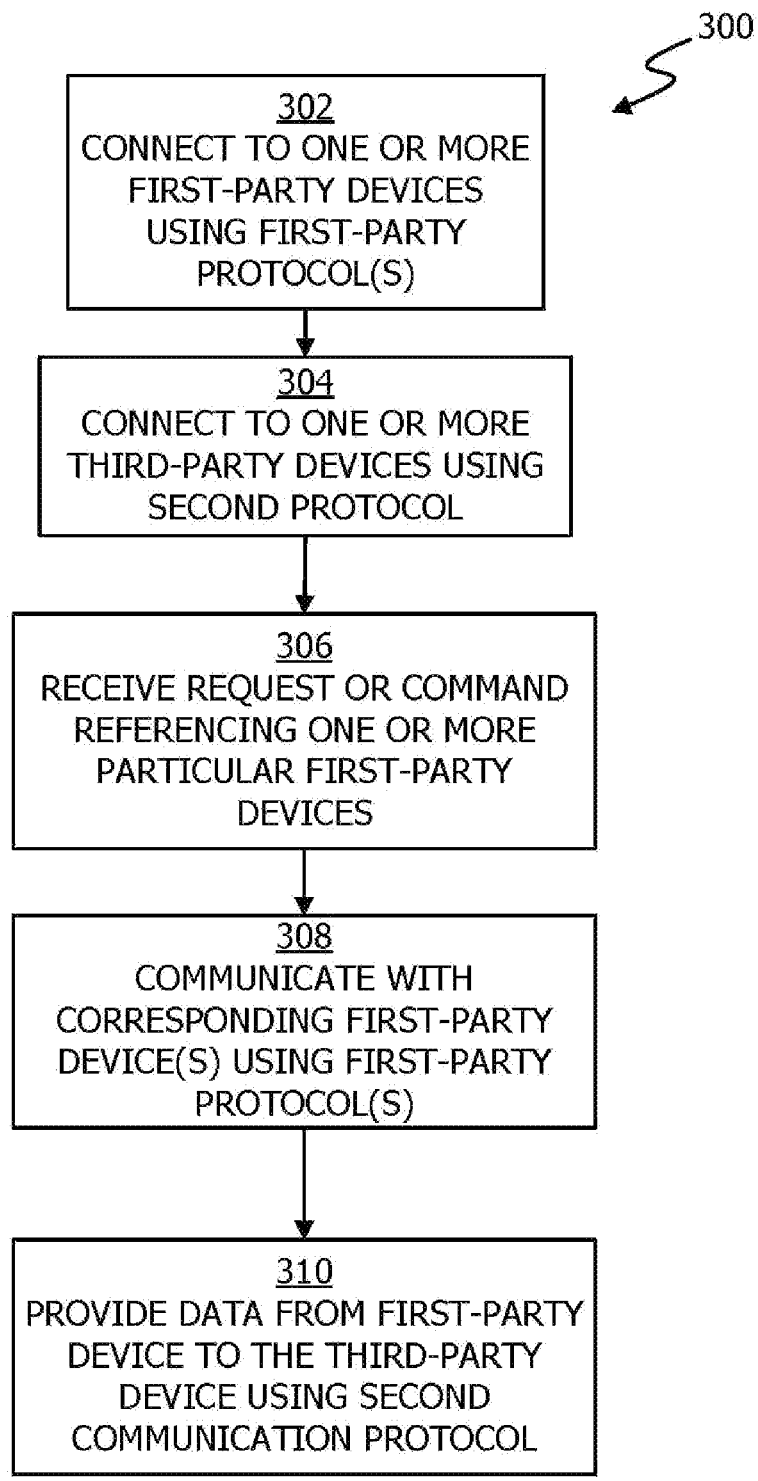
FIG. 3 is a flowchart showing steps of an illustrative method carried out by an interface device.

FIG. 3 is a flowchart showing steps of an illustrative method 300 carried out by an interface device such as device 122. Block 302 represents connecting to the first-party device or devices (e.g., devices 106-118 of FIG. 2), such as verifying the physical connection and carrying out appropriate handshaking according to the first-party communication protocol(s) of the respective first-party device(s). The "first-party devices" can include any medical devices that communicate using a communications protocol defined by an entity separate from an entity that provides a "third-party device." Typically, all first-party devices may originate from the same entity, although it is possible that the first-party devices could include devices from manufacturers of a group that shares a communications protocol in a controlled manner. As noted above, the first-party devices may all share a common, but proprietary, protocol or various first-party devices may utilize distinct first-party protocols.

Block 304 represents connecting to the third-party device or devices (e.g., device 120 of FIG. 2) according to the second communications protocol. In one embodiment, block 304 comprises establishing a client-server relationship, with the second communications protocol specifying a set of polling and error-handling rules to ensure that the link to the third-party device(s) remains viable. The second communications protocol is different from the first-party protocol (or protocols) and the details of the second communications protocol can be made available to providers of third-party devices.

While the link to the third-party device remains viable, the interface device can respond to requests made by the third-party device and identifying particular devices or functions. This is represented in FIG. 3 at blocks 306, 308, and 310.

Block 306 represents receiving a request or command referencing a particular first-party device. For instance, in one embodiment each first-party device or function is assigned a unique TCP/IP port number and thus can be referenced in terms of the TCP/IP port number used by the third-party device in providing a request and receiving data.

Block 308 represents communicating with the corresponding first-party device(s) using the respective first-party protocol or protocols, such as by providing a request or command to the corresponding device over the appropriate first-party interface. Block 308 may further comprise receiving data from the first-party device(s). Block 310 represents providing data from the first-party device(s) according to the second communications protocol. For example, data from the first-party device(s) may be converted as appropriate and then sent to the third-party device. The data may comprise a status update, confirmation of a setting change, etc. In some embodiments, data and messages related to particular first-party device are relayed by the interface device using a TCP/IP port specifically associated with that first-party device.

In some embodiments, the interface device receives a command at block 306, converts the command to the appropriate first-party protocol, and then at block 308 relays the command to the first-party device, which then returns data in response. The returned data can then be converted and sent to the third-party device at block 310. However, as explained below, in some embodiments the interface device operates on an "ask-me" basis and communicates with the first-party and third-party devices using parallel processes—the interface device periodically polls the first-party device(s) and has cached data ready from each device for when a request is received from the third-party device(s).

In addition to or instead of polling the first-party devices, data may be provided by the first-party devices in "unsolicited updates" to the interface device. Similarly, in addition to or instead of waiting for requests from the third-party device, the interface device may provide unsolicited updates to the third-party device in response to receipt of updated data from one or more first-party devices.

Figure 4:
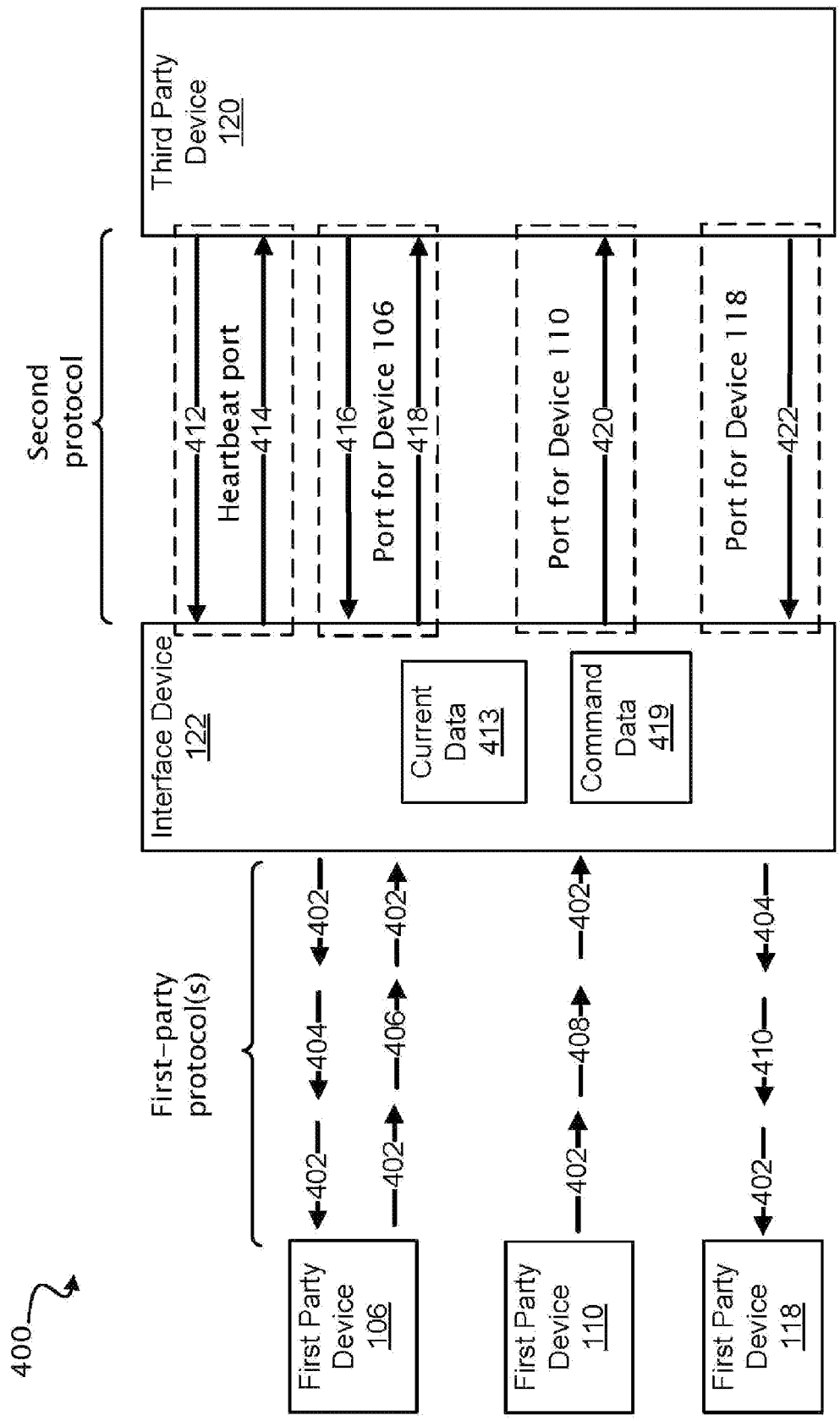
FIG. 4 is a data flow diagram showing exchange of data between the first-party medical devices, an interface device, and a third-party device.

FIG. 4 is a data flow diagram 400 showing exchange of data between three of the first-party medical device(s) (106, 110, and 118), the interface device 122, and the third-party device(s) 120. Three first-party devices are shown here for ease of explanation, though of course the principles are applicable regardless of the number of devices.

In this example, interface device 122 is providing data to device 106, which is responding. In particular, handshaking data 402 is interleaved with a command 404 provided by interface device 122 and device 106 responds with interleaved handshaking data 402 and response data 406. A handshaking routine may be used initially to establish communication with each of the first-party devices according to one or more first-party protocols. For example, this can comprise verifying the physical link, authenticating the device 106 as authorized, and otherwise readying a data communications channel according to the first-party protocol for each device. Handshaking data 402 can also be interleaved with commands and responses as shown here so that the integrity of the communications link is verified. The particular handshaking and data protocol (i.e., the first-party protocol) will of course depend on the characteristics of the individual devices, and the use of reference numeral 402 is for purposes of illustration only and is not intended to imply that all devices use the same handshaking data/protocol.

Although interface device 122 can poll the first-party devices, the first-party devices need not wait for a polling cycle to provide updates. Instead, as shown at first-party device 110, embodiments can support receipt of a datastream comprising unsolicited update data 408 (interleaved in this example with handshaking data 402). For example, first-party device 110 may have a status update based on internal conditions of the device and/or an external condition monitored by the device. The unsolicited update can be received by interface device 122 and used to update current data set 413.

First-party device 118 is shown receiving an interleaved data stream including handshaking data 402, a polling request 410, and a command 404. This example shows how various combinations of handshaking, polling, and commands can be used as appropriate for the various first-party devices.

Interface device 122 also performs a handshaking routine with third-party device 120 but according to the second communications protocol. For example, in one embodiment interface device 122 establishes a full TCP/IP communication stack as noted above. In this example, a dedicated TCP/IP "heartbeat port" is shown, with communication verified by messages 412 and 414 between third-party device 120 and interface device 122. By ensuring that the communication link between devices 120 and 122 is intact, device 122 can provide unsolicited updates to third-party controller 120. Thus, if device data and/or status changes, the third-party controller 120 can be updated more quickly rather than waiting for a polling cycle to complete. As an example, if one of the first-party devices comprises a camera or other monitoring tool that encounters an error and drops off from communication, the third-party controller can be immediately updated. If communication via the heartbeat port cannot be verified, then an appropriate error condition can be indicated at third-party device 120—for example, both devices 120 and 122 may attempt to restore the connection, with device 120 indicating that data is not available until the connection is restored.

FIG. 4 shows additional ports using dashed lines, particularly dedicated ports for each of devices 106, 110, and 118. In some embodiments, each device has a corresponding port number which is defined according to the second communications protocol. For example, as shown at 416, third-party device 120 may provide a command according to the second protocol and using the TCP/IP port corresponding to first-party device 106. The command data 419 can be extracted and stored in memory and then provided as a command according to the first-party protocol for the corresponding device. For instance, command data 419 may be translated to the stream 402-404-402 provided to first-party device 106. In response, data from the 402-406-402 data stream may be used to update current data 413 and then provided according to the second protocol as shown at 418.

Interface device 122 also provides a TCP/IP port that corresponds to first-party device 110. For example, the unsolicited update (shown at 402-408-402) can be used by interface device 122 to update current data 413. In response to the occurrence of the update, interface device 122 can itself provide an unsolicited update to third-party device 120 via the port for device 110 as shown at 420.

In this example, there is also a port for device 118. For instance, third-party device 120 may provide a command and request for data using the port as shown at 422. In response, interface device 122 updates command data and issues the 402-410-404 data stream noted above. For example, in FIG. 2 a request from device 120 may be a request for data from one or more devices and/or may comprise command(s) for the devices, such as a request from device 120 comprising a command to fluid management system 118 to increase or decrease a flow rate. In one embodiment, device 120 issues the request on the TCP/IP port number dedicated to fluid management system 118 along with data identifying the command according to a published syntax for the second communications protocol. As an example, the command for increasing flow rate may comprise an ASCII message stating "Flow++".

In FIG. 2, processor 138 can identify that the command is intended for fluid management system 118 based on the port number of the client request from device 120. Processor 138 can convert the ASCII message into a suitable command syntax for fluid management system 118 and relay the command over link 132 using the specific protocol for fluid management system 118. The next time fluid management system 118 is polled or provides an unsolicited update according to the first-party protocol, the data it provides will reflect its response to the command.

As another example, in some embodiments a device (such as device 112 of FIG. 2) may be configured to display image data. Device 120 can request current image data from camera system 112 by providing a request over the port number for camera system 112 and suitable syntax identifying the desired data (e.g., an ASCII message stating "Update Image( )"). In response, interface device 122 can relay the command/request over link 130, receive the current data, and then provide the current data over link 136. Additionally or alternatively, camera system 112 (or another device) may provide current data to interface device 122 in response to periodic queries or pings provided by interface device 122. The current data can be cached in memory 140 of interface device 122 for easy access by device 120 via 136.

The datastreams between the first-party devices were discussed in sequence above, and in some embodiments a sequence of polling or parallel polling could be used. However, embodiments include those in which interface device 122 supports multitasking and therefore various communications can occur simultaneously between interface device 122 and the different first-party devices. Similarly, communications between interface device 122 and third-party device 120 may also occur simultaneously (and at the same time as communications between device 122 and the first-party devices).

As an example in FIG. 4, third-party device 120 may receive data as shown at 418 and 420 at the same time via the respective ports. During this time period, communications 412 and 414 may occur via the heartbeat port to ensure a viable connection. Also during this time period, interface device 122 may be providing and/or receiving data unrelated to the data shown at 418 and 420—for example, while interface device provides data 418 and 420, even newer data may be en route from the respective first-party device that provided the data, and still further commands may be provided to other first-party devices via their respective connections.

For purposes of clarity, separate datastream components are not shown at 416, 418, 420, and 422. It will be understood that, within the individual ports, suitable handshaking can occur to ensure the viability of the port and the integrity of data exchanged according to the second protocol.

Figure 5A:
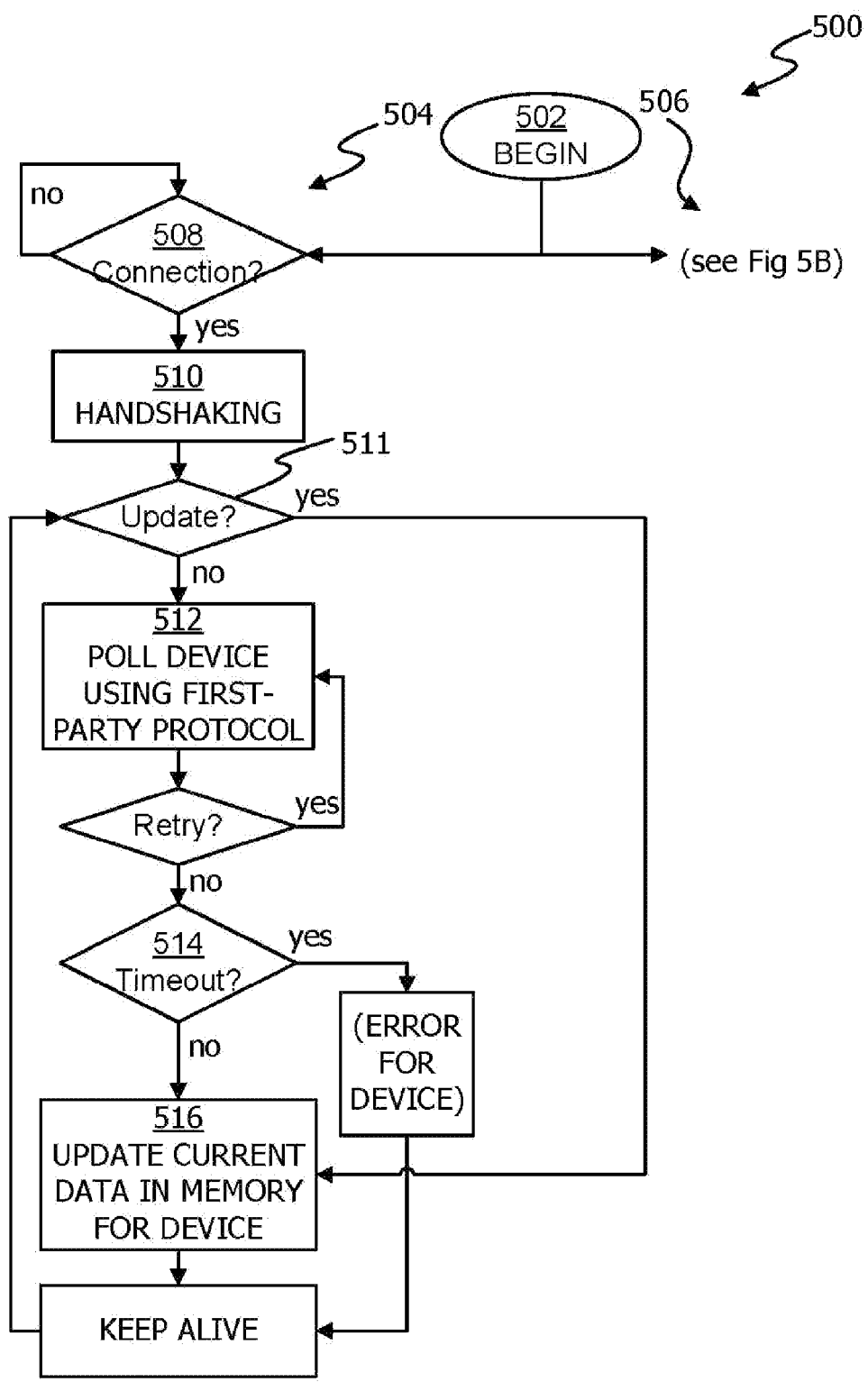
FIGS. 5A-5B are a flowchart illustrating an illustrative processing method that can be carried out by an interface device.
Figure 5B:
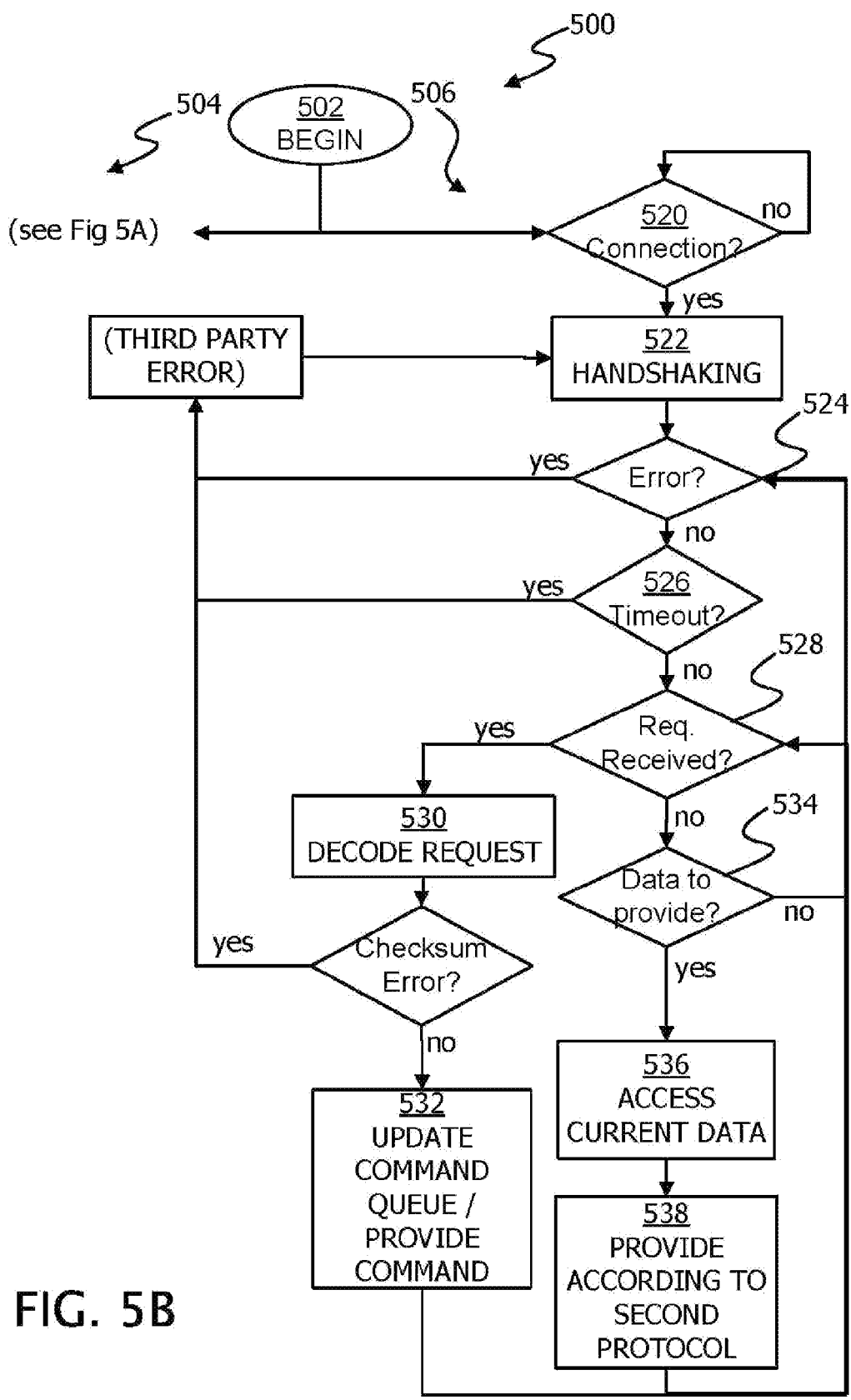

FIGS. 5A-5B are a flowchart illustrating an illustrative processing method 500 that can be carried out by an interface device. Although the general principle was discussed above in conjunction with FIG. 3, FIGS. 5A-5B provide a more detailed example that may be used to provide the robust connectivity and updates demanded in many medical contexts. In this example, method 500 begins at 502 and includes two parallel branches 504 (shown in FIG. 5A) and 506 (shown in FIG. 5B). If the processor of the interface device can carry out parallel threads, each branch may comprise its own thread, or the branches could be implemented using a multitasking-capable processor. Additionally, the processor may provide an instance of branch 504 for each first-party device, with the different instances of branch 504 used for simultaneous connection with the connected device.

Each instance of branch 504 represents communication with a respective first-party devices. Block 508 represents determining if the first-party device is connected. This can comprise determining if a physical connection is present based on line voltage levels, impedance, etc. as is known in the art. If the device is connected, then at block 510 appropriate handshaking can be performed to establish an initial connection.

At block 511, the method checks for an update message from the device. If the device has provided an unsolicited update, then the method moves to block 516, which represents updating current data in memory of the interface device based on data returned from the first-party device and is discussed below. If no data has been received from the device, then the method moves to block 512, which represents polling the device by sending a "ping" or other recognizable message to the device according to the first-party device protocol.

In one embodiment, each first-party device is polled every 250 milliseconds, though of course other time intervals could be used, and a number of retries may be attempted. Accordingly, FIG. 5A includes a retry block to represent determining whether a retry is needed. If so, then flow returns to block 512. Otherwise, if no retry is needed flow moves to block 514, which represents determining if there is a device timeout or if a device provides an unexpected or unintelligible response. If so, then an appropriate error-handling routine can be triggered—for example, a limited number of retries of the entire polling sequence may be attempted before an error condition is provided. Flow then moves to providing the "keep alive" command while branch 504 regresses one level to attempt polling again at block 512. In one embodiment, after four attempts of the polling sequence (with each attempt exhausting the number of retries and also resulting in a timeout) the method returns to block 510 to attempt to identify the device again.

However, if the polled device responds to the polling at block 512 (i.e., there is no timeout at block 514), then block 516 is reached. Block 516 represents updating current data in memory of the interface device based on data returned from the first-party device. The interface device is configured to recognize the data format and communications protocol of each first-party device and to store the returned data in memory. The data may be stored using a format internal to the interface device, in the format as provided according to the first-party protocol, or may be converted and stored according to the second communications protocol. Appropriate error-handling routines can be used to verify the response as noted above—for instance, if checksum data or other coding indicates a problem, an error state may be indicated. The "keep alive" request is also provided and then flow returns to blocks 511-512 to again check for data and poll the device if needed.

In some embodiments, all of the connected first-party devices can be connected and communicated with according to branch 504. However, in other embodiments, devices can be polled in turn. Additionally, the routine can include appropriate handling of device connections/disconnections—when a new device is connected, the polling sequence can begin and when a device is disconnected appropriate steps can be taken to end the polling process. In practice, the handshaking and keep alive requests can interleave with the status and service updates once a connection has been established.

If a command is to be provided to a first-party device, the command can be provided when the device is polled or as a separate message to the device. This can be carried out because the interface device understands the communications protocol of the first-party device. For example, power level commands for a particular device may be specified at a particular offset in the command message and/or may require a particular bit sequence to trigger the command. When such a command is to be provided, the interface device can construct the appropriate bitstream and include the bitstream in an appropriately-timed message.

Method 500 also includes branch 506, which represents maintaining an interface for communications with a third-party device according to a second protocol. In contrast to the protocol or protocols of the first-party device(s), which are kept proprietary, the second protocol can be shared with third-party manufacturers. Additionally, the second protocol is not device-specific; instead, the second protocol can be used to exchange data for a plurality of different devices (e.g., for all of the first-party devices connected to the interface device).

Block 520 represents determining if a third-party device is connected to the port(s) that provide communications using the second protocol. For example, if a RJ45 connection is to be used, block 520 can represent determining if a physical connection is present. Block 522 represents handshaking and setting up an appropriate network communications channel over the connection. In some embodiments, this comprises establishing a network socket connection, such as a TCP/IP socket connection, along with opening TCP/IP ports corresponding to each connected first-party device. Blocks 524 and 526 represent determining if an error occurs during/after handshaking process or if there is a timeout. If so, flow returns to block 522 to attempt handshaking again.

For example, the third-party equipment may be expected to "check in" at least every 250 milliseconds, though of course a different time interval could be specified. Accordingly, in some embodiments the interface device is configured to allocate a network port (e.g., a TCP/IP port) as a "heartbeat" port for use in monitoring a status of the connection to the third-party device in order to ensure an ongoing connection. Blocks 524-526 may occur continuously based on messages exchanged over a "heartbeat" port, and represent more generally determining whether at least a request over the heartbeat TCP/IP port has been received. If no heartbeat is detected, the interface device can respond to an error condition.

If there are no errors/timeouts, the method moves to block 528, which represents determining if a request for data or a command has been received from the third-party device. If a request is received at block 528, the method moves to block 530, which represents decoding the request. The second communications protocol can specify a syntax for addressing devices and formatting requests for data, device commands, and the like and the interface device can recognize that syntax. For example, the request can be made over a particular TCP/IP port number for a specific device and can comprise a command and/or a request for one or more data items. Therefore, block 528 is meant to include monitoring several TCP/IP ports simultaneously. In practice, several threads may be maintained, each thread for coordinating requests and responses over a corresponding TCP/IP port.

Returning to FIG. 5B, a checksum or other error correction routine check can be made. In this example, if there is a checksum error then flow returns to block 522 via the error state to attempt handshaking again. Assuming no checksum error, requests for data and/or commands can be processed as shown at block 532. For a request for data item(s) the interface device stores the command in a queue so that the command is provided to the device at the next polling interval. The command may be stored using a format internal to the interface device, in the format as provided according to the second communications protocol, or may be converted and queued in the first-party protocol. If the request comprises a command, the interface device may directly respond by converting the command for transmission using the first-party protocol shortly after the command is received.

Returning to block 528, in this example if no request has been received (or if a received request has been processed), the method moves to block 534, which represents determining if there is data to provide. As noted above, in some embodiments the interface device can provide unsolicited updates so that the third-party equipment has the most up-to-date data. As an example, the device may use timestamps and/or status bits associated with data items received from the first-party equipment to determine if the data items have been provided to the third party equipment.

If there is data to provide, the data is accessed at block 536 and then provided at block 538 in a format according to the second communications protocol. As noted above, the data may be stored using the original data format or may be converted at the time of storage. In any event, the interface device is capable of converting the data because the interface device understands the first-party communications protocol and the protocol used for communicating with the third-party device. For example, the protocol for a particular device may specify that device status information (e.g., device power level, temperature, etc.) is included at a particular offset in a serial data stream using a particular bit pattern. The interface device can be programmed to identify the device status information in the serial data sequence, translate the bit pattern, and to store the status information in memory. When it is time to convert the data, the interface device can construct a message according to the syntax of the second communications protocol and then send the message appropriately (e.g., by sending an ASCII message over the TCP/IP port corresponding to the device whose status is being updated).

The method shown in FIGS. 5A-5B is provided for purposes of illustration only. For instance, embodiments may return current data in response to queries from the third party device. For example, if the request at block 530 is for current data, then at block 532 the interface device can provide a query for updated data item(s) over the first interface using the first-party protocol and, when updated data is returned, the data can be converted for transmission using the second protocol at blocks 536 and 538.

In practice, the interface device can also carry out suitable routines to enter and exit the polling and data exchange routines upon error and other events such as device shutdown. Additionally, the interface device can support administrative and security processes as well.

In one embodiment, the interface device includes an authentication routine for verifying access via the second interface and/or to provide administrative commands to the interface device. For example, the various first-party device ports may be enabled or locked in response to administrative commands, network options may be set, and device parameters may be adjusted. In some embodiments, the administrative interface can be used to update the interface device programming to support additional first-party devices and/or changes to supported first-party communications protocols.

General Considerations

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. In one embodiment, a computer may comprise a processor or processors. The processor comprises or has access to a computer-readable medium, such as a random access memory (RAM) coupled to the processor. The processor executes computer-executable program instructions stored in memory, such as executing one or more computer programs to interact with first-party and third-party equipment as noted above.

Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible and non-transitory computer-readable media, that may store instructions that, when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a server, with computer-readable instructions.

Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing, described may be in one or more structures, and may be dispersed through one or more structures. The processor may comprise code for carrying out one or more of the methods (or parts of methods) described herein.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed:

1. An apparatus, comprising:
   a processor;
   a memory;
   a plurality of first hardware connection ports each configured to connect to a corresponding data interface of a medical device; and
   at least one second hardware port configured to connect to a third-party device,
   wherein the memory embodies program instructions that configure the processor:
   to recognize at least one first-party communication protocol used to communicate with one or more of the medical devices via the first hardware connection ports;
   to recognize a second communication protocol used to communicate with the third-party device via the second hardware port;
   to concurrently receive, via at least one of the first hardware connection ports, data from each of the medical devices in a first format according to the at least one first-party communication protocol;
   to store the data received from each of the medical devices in the memory in a third format internal to the apparatus;

to translate the data from the third format internal to the apparatus to a second format according to the second communication protocol; and to provide, via the second hardware port, the data to the third-party device in the second format according to the second communication protocol, wherein the first format according to the at least one first-party communication protocol, the second format according to the second communication protocol, and the third format internal to the apparatus are different formats.

2. The apparatus set forth in claim 1, wherein the program instructions configure the processor to:

receive data from the third-party device in the second format according to the second communication protocol, the data identifying a command for at least one of the medical devices;

store the data identifying the command in the memory; and provide the command to at least one of the medical devices in the first format according to the at least one first-party communication protocol based on the stored data.

3. The apparatus set forth in claim 1, wherein the program instructions configure the processor to:

establish a network socket connection with the third-party device;

associate a network port with each connected medical device; and provide the data from the medical device associated with the network port, the data returned in the second format according to the second communication protocol and using the network port associated with the medical device.

4. The apparatus set forth in claim 1, wherein the program instructions configure the processor to:

establish a network socket connection with the third-party device;

allocate a network port for monitoring a status of the connection to the third-party device; and respond to an error condition if a request identifying the allocated network port is not received within a timeout interval.

5. The apparatus set forth in claim 3, wherein the network socket connection is a TCP/IP socket connection and the network port is a TCP/IP port.

6. The apparatus set forth in claim 4, wherein the network socket connection is a TCP/IP socket connection and the network port is a TCP/IP port.

7. The apparatus set forth in claim 1, further comprising:

a plurality of medical devices, each medical device connected to a respective one of the first hardware ports; and a third-party medical device connected to the at least one second hardware port and configured to perform at least one of providing data to or receiving data from the plurality of medical devices by communicating via the second hardware port, wherein the third-party medical device is configured to communicate using the second communication protocol but not the at least one first-party communication protocol.

8. The apparatus set forth in claim 1, further comprising:

a plurality of medical devices, each medical device connected to a respective one of the first hardware ports; and a third-party medical device connected to the at least one second hardware port and configured to perform at least one of providing data to or receiving data from the plurality of medical devices by communicating via the second hardware port, wherein the third-party medical device is configured to communicate using the second communication protocol but not the at least one first-party communication protocol.

9. The apparatus set forth in claim 2, further comprising:

a plurality of medical devices, each medical device connected to a respective one of the first hardware ports; and a third-party medical device connected to the at least one second hardware port and configured to perform at least one of providing data to or receiving data from the plurality of medical devices by communicating via the second hardware port, wherein the third-party medical device is configured to communicate using the second communication protocol but not the at least one first-party communication protocol.

10. The apparatus set forth in claim 3, further comprising:

a plurality of medical devices, each medical device connected to a respective one of the first hardware ports; and a third-party medical device connected to the at least one second hardware port and configured to perform at least one of providing data to or receiving data from the plurality of medical devices by communicating via the second hardware port, wherein the third-party medical device is configured to communicate using the second communication protocol but not the at least one first-party communication protocol.

11. The apparatus set forth in claim 4, further comprising:

a plurality of medical devices, each medical device connected to a respective one of the first hardware ports; and a third-party medical device connected to the at least one second hardware port and configured to perform at least one of providing data to or receiving data from the plurality of medical devices by communicating via the second hardware port, wherein the third-party medical device is configured to communicate using the second communication protocol but not the at least one first-party communication protocol.

12. The apparatus set forth in claim 1, wherein the processor is configured to recognize a plurality of first-party communication protocols, each one of the plurality of first-party communication protocols corresponding to a particular medical device.

13. The apparatus set forth in claim 1, wherein the processor is configured to recognize a plurality of first-party communication protocols, each one of the plurality of first-party communication protocols corresponding to a particular medical device.

14. The apparatus set forth in claim 2, wherein the processor is configured to recognize a plurality of first-party communication protocols, each one of the plurality of first-party communication protocols corresponding to a particular medical device.

15. The apparatus set forth in claim 3, wherein the processor is configured to recognize a plurality of first-party communication protocols, each one of the plurality of first-party communication protocols corresponding to a particular medical device.

16. The apparatus set forth in claim 4, wherein the processor is configured to recognize a plurality of first-party communication protocols, each one of the plurality of first-party communication protocols corresponding to a particular medical device.

17. The apparatus set forth in claim 1, wherein at least some of the first hardware connection ports comprise serial ports and wherein the second hardware port comprises a network connection port.

18. The apparatus set forth in claim 1, wherein at least some of the first hardware connection ports comprise serial ports and wherein the second hardware port comprises a network connection port.

19. The apparatus set forth in claim 2, wherein at least some of the first hardware connection ports comprise serial ports and wherein the second hardware port comprises a network connection port.

20. The apparatus set forth in claim 3, wherein at least some of the first hardware connection ports comprise serial ports and wherein the second hardware port comprises a network connection port.

21. The apparatus set forth in claim 4, wherein at least some of the first hardware connection ports comprise serial ports and wherein the second hardware port comprises a network connection port.

22. The apparatus set forth in claim 1, wherein the processor is configured to communicate with the plurality of first hardware connection ports using a first bus and to communicate with the at least one second hardware port using a second bus.

23. The apparatus set forth in claim 1, wherein the processor is configured to communicate with the plurality of first hardware connection ports using a first bus and to communicate with the at least one second hardware port using a second bus.

24. The apparatus set forth in claim 2, wherein the processor is configured to communicate with the plurality of first hardware connection ports using a first bus and to communicate with the at least one second hardware port using a second bus.

25. The apparatus set forth in claim 3, wherein the processor is configured to communicate with the plurality of first hardware connection ports using a first bus and to communicate with the at least one second hardware port using a second bus.

26. The apparatus set forth in claim 4, wherein the processor is configured to communicate with the plurality of first hardware connection ports using a first bus and to communicate with the at least one second hardware port using a second bus.

27. The apparatus set forth in claim 1 wherein the memory further embodies program instructions that configure the processor:
   to receive, via the second hardware port, a command from the third-party device in the second format according to the second communication protocol;
   to store the command in the memory;
   to translate the command to the first format according to the at least one first-party communication protocol; and
   to provide, via the at least one of the first hardware connection ports, the command to the at least one of the medical devices in the first format according to the at least one first-party communication protocol.

28. The apparatus set forth in claim 27 wherein the memory further embodies program instructions that configure the processor to store the command in the memory in a third format internal to the apparatus.

29. The apparatus set forth in claim 28 wherein the memory further embodies program instructions that configure the processor to translate the command from the third format internal to the apparatus to the first format according to the at least one first-party communication protocol.

30. The apparatus set forth in claim 1 wherein the memory further embodies program instructions that configure the processor to store the data in the memory in the first format according to the at least one first-party communication protocol.

31. The apparatus set forth in claim 30 wherein the memory further embodies program instructions that configure the processor to translate the data from the first format according to the at least one first-party communication protocol to the second format according to the second communication protocol.

32. The apparatus set forth in claim 1 wherein the memory further embodies program instructions that configure the processor:
   to translate the data from the first format according to the at least one first-party communication protocol to the second format according to the second communication protocol; and
   to store the data in the memory in the second format according to the second communication protocol.

33. An apparatus for providing interoperability among a plurality of medical devices, the plurality of medical devices each having a corresponding data interface, the apparatus comprising:
   a plurality of ports, each port being operative to connect to the corresponding data interface of a respective medical device;
   at least one memory; and
   at least one processor operative to execute at least one computer program out of the at least one memory:
      to receive, from each of at least some of the plurality of medical devices, information pertaining to one or more of a data format, a syntax, and one or more settings employed by the respective medical device, wherein the information received from the respective medical device is indicative of one or more of (1) input data that the respective medical device is capable of receiving from at least another one of the plurality of medical devices, (2) output data that the respective medical device is capable of providing to the other one of the plurality of medical devices, and (3) one or more control messages that the respective medical device is capable of accepting from the other one of the plurality of medical devices; and
      to establish, over the port connected to the corresponding data interface of the respective medical device, a communication link between the respective medical device and the other one of the plurality of medical devices using at least some of the information received from the respective medical device;
      to concurrently receive the output data from the respective medical device and at least the other one of the plurality of medical devices;
      to store the output data receive from the respective medical device and the other one of the plurality of medical devices in the at least one memory;
      to provide the output data received from the respective medical device as the input data to the other one of the plurality of medical devices; and
      to provide the output data received from the other one of the plurality of medical devices as the input data to the respective medical device, wherein one or more of concurrently receiving the output data, storing the output data, providing the output data received from the respective medical device, and providing the output data received from the other one of the plurality of medical devices are performed based on at least some of the information used to establish the communication link between the respective medical device and the other one of the plurality of medical devices, and wherein the providing of the output data received from the respective medical device as the input data to the other one of the plurality of medical devices is further performed without the other one of the plurality of medical devices soliciting the output data from the respective medical device.

34. The apparatus of claim 33 wherein the providing of the output data received from the other one of the plurality of medical devices as the input data to the respective medical device is performed without the other one of the plurality of medical devices being solicited by the respective medical device to provide the output data.

35. A method of providing interoperability among a plurality of medical devices, the plurality of medical devices each having a corresponding data interface, the method comprising:

receiving, at a computerized apparatus from each of at least some of the plurality of medical devices, information pertaining to one or more of a data format, a syntax, and one or more settings employed by the respective medical device, the information being indicative of one or more of (1) input data that the respective medical device is capable of receiving from at least another one of the plurality of medical devices, (2) output data that the respective medical device is capable of providing to the other one of the plurality of medical devices, and (3) one or more control messages that the respective medical device is capable of accepting from the other one of the plurality of medical devices;

establishing, by the computerized apparatus over a port connected to the corresponding data interface of the respective medical device, a communication link between the respective medical device and the other one of the plurality of medical devices using at least some of the information received from the respective medical device; and performing, based on at least some of the information used to establish the communication link with the respective medical device, one or more of:

concurrently receiving, at the computerized apparatus, the output data from the respective medical device and at least the other one of the plurality of medical devices;

storing, by the computerized apparatus, the output data received from the respective medical device and the other one of the plurality of medical devices in at least one memory;

providing, by the computerized apparatus, the output data received from the respective medical device as the input data to the other one of the plurality of medical devices without the other one of the plurality of medical devices soliciting the output data from the respective medical device; and providing, by the computerized apparatus, the input output data received from the other one of the plurality of medical devices as the input data to the respective medical device.

36. The method of claim 35 wherein the providing of the output data received from the other one of the plurality of medical devices to the respective medical device is performed without the other one of the plurality of medical devices being solicited by the respective medical device to provide the output data.

* * * * *